United States Patent
Popkova et al.

(10) Patent No.: US 6,175,042 B1
(45) Date of Patent: Jan. 16, 2001

(54) PROCESS FOR PREPARING PERFLUOROALKYL ARYL SULFIDES AND NOVEL PERFLUOROALKYL ARYL SULFIDES

(75) Inventors: Vera Yakovlevna Popkova, Moscow (RU); Albrecht Marhold, Leverkusen (DE)

(73) Assignee: Bayer Aktiengesellschaft, Leverkusen (DE)

(*) Notice: Under 35 U.S.C. 154(b), the term of this patent shall be extended for 0 days.

(21) Appl. No.: 09/322,619

(22) Filed: May 28, 1999

(30) Foreign Application Priority Data

Jun. 2, 1998 (DE) .............................. 198 24 488

(51) Int. Cl.$^7$ ................................. C07C 321/20
(52) U.S. Cl. ................. 564/440; 568/56; 568/55
(58) Field of Search ................ 568/38, 39, 51, 568/55, 56; 564/440, 442; 546/290; 544/298

(56) References Cited

U.S. PATENT DOCUMENTS

| | | |
|---|---|---|
| 3,790,681 * | 2/1974 | Bulteau . |
| 4,581,059 | 4/1986 | Adams, Jr. et al. ..................... 71/92 |
| 4,960,789 | 10/1990 | Wollweber et al. ................. 514/427 |
| 5,015,757 | 5/1991 | Wollweber et al. ................. 558/401 |
| 5,082,945 | 1/1992 | Wakselman et al. ................ 546/110 |
| 5,283,337 | 2/1994 | Wakselman et al. ................ 546/279 |
| 5,756,849 | 5/1998 | Forat et al. ............................ 568/27 |

FOREIGN PATENT DOCUMENTS 3737985   5/1989  (DE) .

OTHER PUBLICATIONS

Chemistry Letter, (month unavailable) 1990, pp. 2269–2272, Benzentetellurinic Mixed anhydrides as mild oxidizing Agents$^{1)}$, Takahiro Fukumoto et al.

J. Org. Chem. USSR, 20, pp. 181–182, (month unavailable) 1984, Synthesis of 2,7–Dinitro– and 2,7–Diaminothianthrene, V.N. Lisitsyn et al.

Khim Geterots, Soed, No. 9, (month unavailable) 1992, A.B. Ahncnmob et al, pp. 1276–1279.

J. General Chem. USSR, vol. 13, (month unavailable) 1983, pp. 2254–2258, Acid–Base Properties of (Perfluoroalkylthio)– and (Perfluoroalkylsulfonyl)–Substituted Benzoic Acids N.V. Kondratenko et al.

Tetrahedron Letters, vol. 37, No. 50 (month unavailable) 1996, pp. 9057–9058, A Convenient synthesis of Trifluoromethyl Aryl Sulfides, Beatrice Quicletc–Sire$^a$ et al.

J. Or. Chen. USSR, No. 13, (month unavailable) 1977, pp. 1985–1988, Radical–ion Perfluoroalkylation of Aromatic Thiols, V.I. Popov et al.

Synthetic Commun., 26(1), (month unavailable) 1996, pp. 191–196, Preparation of Disulfides by the Oxidation of Thiols Using Bromine, Xiaoming Wu et al.

Synthetis Commun., 25(2), (month unavailable) 1995, pp. 227–234, Sodium Chlorite—Yet another Oxidant for Thiols to Disulphides.

Chem. Heteroc. Comp., 28, (month unavailable) 1992, pp. 1084–1086, formation of Benzothia Crowns in Reaction of the Diallyl Derivative of 2–Mercapto–4–Methylphenol.

J. Org. Chem., vol. 59, No. 15, (month unavailable) 1994, p. 4047, Communictions.

Clark et al, Aromatic Fluorination, CRC Press Boca Raton, (month unavailable) 1996, pp. 119–138, Trifluoromethylthioaromatics and Trifluoromethylsulfonuylaromatics.

CA: 107:39371 abs of FR 2579592, Oct. 1986.*
CA:84:30585 abs of Synthesis 11 pp 721–3 by Yagupol'skii et al., 1975.*
CA:91:5662 abs of DE2745006, Apr. 1979.*
CA:111:117890 abs of Appl Catal 52(1–2) pp 57–68 by Tropainen, 1989.*

* cited by examiner

*Primary Examiner*—Jean F Vollano
(74) *Attorney, Agent, or Firm*—Joseph C. Gil; Richard E.L. Henderson

(57) ABSTRACT

This invention relates to a process for preparing perfluoroalkyl aryl sulfides by reaction of disulfides with alkali metal salts of aliphatic perfluorocarboxylic acids in the presence of a high-boiling aprotic solvent at elevated temperature and reduced pressure, wherein the product formed is distilled off at the rate at which it is formed. This invention further relates to the novel compounds 2-nitrophenyl pentafluoroethyl sulfide and 2-aminophenyl pentafluoroethyl sulfide.

2 Claims, No Drawings

PROCESS FOR PREPARING PERFLUOROALKYL ARYL SULFIDES AND NOVEL PERFLUOROALKYL ARYL SULFIDES

BACKGROUND OF THE INVENTION

The present invention relates to an improved process for preparing perfluoroalkyl aryl sulfides and to two novel perfluoroalkyl aryl sulfides.

Aromatic compounds carrying fluorine-containing substituents are intermediates for the synthesis of agrochemicals, pharmaceuticals, dyes, and polymers. The trifluoromethylthio group in particular is included in the development of novel biologically active compounds and novel dyes, since it has high chemical stability and is the most lipophilic known substituent E.g., R. E. Banks and K. C. Lowe, "Fluorine in Medicine in the 21$^{st}$ "Century", Chemserve Ltd., Manchester (1994); S. B. Walker, "Fluorine Compounds as Agrochemicals", Fluorochem Ltd., Old Glossop (U.K.) (1990); EP-A 374,061; J. H. Clark, D. Wails, and T. W. Bastock, "Aromatic Fluorination", CRC Press, Boca Raton, Fla. (1996), page 119. 2-Hydroxyphenyl trifluoromethyl sulfide, for example, is required for preparing certain herbicides. E.g., U.S. Pat. No. 4,581,059. Chlorine-, nitro-, and amino-substituted phenyl trifluoromethyl sulfides are employed as intermediates for pesticides. E.g., DE-A 3,737,984 and DE-A 3,737,985.

Hitherto, a number of methods for preparing perfluoroalkyl aryl sulfides have been disclosed. Most of these methods require expensive and/or toxic reagents, which is a disadvantage for industrial production. Pentafluoroethyl and long-chain perfluoroalkyl radicals can be introduced into aromatic thiols by ion-radical and cationic reactions with perfluoroalkyl iodides. E.g., *J. General Chem. USSR*, 53, 2254 (1983) and *J. Org. Chem. USSR*, 13, 1985 (1977). However, perfluoroalkyl iodides have the disadvantage that they must be prepared in a complicated manner and are therefore expensive.

A more recent method for preparing $C_1$ derivatives in which a thermally induced decarboxylation of potassium trifluoroacetate is carried out in the presence of aryl sulfides has been reported. E.g., *Tetrahedron Lett.*, 37, 9057 (1996). Although this process constitutes a considerable advance on the earlier methods, the yields—in most cases only about 50% of theory—are still unsatisfactory, and the process has hitherto been limited to introducing the trifluoromethyl group. Furthermore, this process is virtually impossible to carry out on an industrial scale, since the strongly exothernic reaction is virtually impossible to control. The entire reaction mixture is described as being heated rapidly by bringing it into contact with a hot heat exchange medium. A strongly exothermic reaction then results. No details about the pressure are given. Consequently, one skilled in the art must assume that the operation was carried out under atmospheric pressure.

SUMMARY OF THE INVENTION

This invention, accordingly, provides a process for preparing perfluoroalkyl aryl sulfides of the formula (I)

$$Ar\text{—}S\text{—}R^f \quad (I),$$

in which

Ar represents optionally substituted phenyl, naphthyl, pyridyl, or pyrimidyl having a molecular weight, excluding any fluorine atoms that may optionally be present, of less than 200 g/mol, and $R^f$ represents a perfluoroalkyl radical having 1 to 7 carbon atoms, comprising (1) reacting disulfides of formula (II)

$$Ar\text{—}S\text{—}S\text{—}Ar \quad (II),$$

in which each Ar is defined as for formula (I), with alkali metal salts of aliphatic perfluorocarboxylic acids of formula (III)

$$R^f\text{—}COO^{(-)}M^{(+)} \quad (III),$$

in which $R^f$ is defined as for formula (I), and

M represents an alkali metal, in the presence of a high-boiling aprotic solvent at elevated temperature and reduced pressure, and (2) distilling off the resultant perfluoroalkyl aryl sulfide of formula (I) at the rate at which it is formed.

Each Ar group preferably represents phenyl, naphthyl, pyridyl or pyrimidyl, each of which is optionally mono- or polysubstituted, independently, by balogen, nitro, cyano, $C_1$–$C_6$-alkyl that is optionally substituted with fluorine and/or chlorine, or $C_1$–$C_6$-alkoxy that is optionally substituted with fluorine and/or chlorine. Each Ar group more preferably represents phenyl, naphthyl or pyridyl, each of which is optionally mono- or polysubstituted, independently, by fluorine, chlorine, bromine, nitro, cyano, $C_1$–$C_4$-alkyl that is optionally substituted with fluorine and/or chlorine, or $C_1$–$C_4$-alkoxy that is optionally substituted with fluorine and/or chlorine. Each Ar group most preferably represents phenyl, naphthyl, 2-pyridyl, 3-pyridyl or 4-pyridyl, each of which is optionally mono- or disubstituted, independently, by fluorine, chlorine, bromine, nitro, cyano, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethoxy, difluoromethoxy, chlorodifluoromethoxy, 2-chloro-1,1,2-trifluoroethoxy, 1,1,2-trifluoroethoxy, 2,2,2-trifluoroethoxy, 1,1,2,2-tetrafluoroethoxy, 2,2,2-trichloro-1,1-difluoroetlioxy, 1,1-difluoroethoxy, trifluoro-methylthio, difluoromethyl, chlorodifluoromethyl, 2-chloro-1,1,2-trifluoroethyl, 1,1,2-trifluoroethyl, 1,1,2,2-tetrafluoroethyl, or pentafluoroethyl.

Group $R^f$ preferably represents a perfluoroalkyl radical having 1 to 5 carbon atoms. Group $R^f$ more preferably represents a perfluoroalkyl radical having 1 to 4 carbon atoms. Group $R^f$ most preferably represents trifluoromethyl, perfluoroethyl, or perfluoropropyl.

The present invention also relates to a process for preparing perfluoroalkyl aryl sulfides of the formula (I')

$$Ar'\text{—}S\text{—}R^f \quad (I'),$$

in which

Ar' represents hydroxyl-, mercapto-, or amino-substituted phenyl, naphthyl, pyridyl, or pyrimidyl having a molecular weight of less than 200 g/mol, and $R^f$ is defied as above for formula (I), comprising (1) reacting disulfides of the formula (II')

$$Ar''\text{—}S\text{—}S\text{—}Ar'' \quad (II'),$$

in which
each Ar" independently represents methoxy-, methylthio-, or nitro-substituted phenyl, naphthyl, pyridyl, or pyrimidyl having a molecular weight of less than 200 g/mol,
with alkali metal salts of aliphatic perfluorocarboxylic acids of the formula (III)
in the presence of a high-boiling aprotic solvent at elevated temperature and reduced pressure, (2) distilling off the resultant compound of formula (I")

Ar"—S—R$^f$ (I")

in which
Ar" is defined as for formula (II'), and
R$^f$ is defined as for formula (I);
at the rate at which it is formed, and (3) forming the perfluoroalkyl aryl sulfides of the formula (I') by (i) cleaving the methoxy or methylthio group of the compound of formula (I") when Ar" represents methoxy- or methylthio-substituted phenyl, naphthyl, pyridyl, or pyrimidyl and/or (ii) reducing the nitro group of the compound of formula (I") when Ar" represents nitro-substituted phenyl, naphthyl, pyridyl, or pyrimidyl.

The molecular weight of the aryl groups Ar, Ar', and Ar", excluding any fluorine atoms that may optionally be present, is preferably less than 180 g/mol (more preferably less than 160 g/mol).

DETAILED DESCRIPTION OF THE INVENTION

The aryl sulfides of formulas (II) and (II') required for carrying out the process according to the invention are commercially available or can be prepared by known or analogous processes. See *Synth. Commun.*, 25, 227 (1995); *Synth. Commun.*, 26, 191 (1996); *Chem. Lett.*, 12, 2269 (1990); *Khim. Geterots. Soed.*, N9, 1276 (1992) [Engl. translation: *Chem Heteroc. Comp.*, 28, 1084 (1992)]; and *Zh. Org. Khim.*, 20, 202 (1984) [English translation.: *J. Org. Chem USSR*, 20, 181 (1984)].

The alkali metal salts of perfluorocarboxylic acids of formula (III) also required as starting materials are also commercially available or can be prepared in a known manner by neutralization from the corresponding perfluorocarboxylic acids. Preference is given to using the sodium or potassium salts (i.e., where M is Na or K), particularly the potassium salts.

In general, 1.0 to 5 mol (preferably 1.5 to 2.5 mol) of an alkali metal salt of a perfluorocarboxylic acid of formula (III) is employed per mole of disulfide of formula (II) or (II').

The processes according to the invention are carried out in the presence of a high-boiling aprotic solvent. Suitable for this purpose are, for example, solvents having a boiling point at atmospheric pressure of above 210° C. (preferably above 250° C.). In principle, there is no upper limit to their boiling point. At the reaction temperature, the solvent should have only a viscosity that is sufficiently low for the reaction mixture to be stirrable. The term "solvent" does not restrict the use to those in which the starting materials are completely soluble at the particular amount used, but the starting materials must be at least partially soluble in the solvents. It is possible, for example, to use tetramethylene sulfone, triethylene glycol dimethyl ether, tetraethylene glycol dimethyl ether, or a high-boiling aliphatic or aromatic hydrocarbon or any mixtures of these solvents. Particular preference is given to tetramethylene sulfone.

When selecting the solvent, it must be ensured that its boiling point at the pressure that is applied is higher than the boiling point of the perfluoroalkyl aryl sulfide of formula (I) or (I') that is to be prepared. In general, 50 to 1000 ml (preferably 100 to 250 ml) of solvent are employed per mole of disulfide of formula (II) or (II').

The processes according to the invention are carried out under reduced pressure. They are generally carried out at from 1 to 500 mbar (preferably from 10 to 300 mbar).

The processes according to the invention are carried out at elevated temperature. In general, they are carried out at from 120 to 250° C. (preferably from 180 to 220° C.).

By routine preliminary experiments, it is easily possible to determining optimum reaction temperatures and pressures for preparing any particular product of formula (I) or (I').

The processes according to the invention can be carried out batchwise, for example, in such a way that the entire amount of the starting materials and the solvent is initially charged, the pressure is reduced, and the mixture is then heated (for example, to from 120 to 150° C.) and then slowly heated further until the reaction has gone to completion. It is possible to further reduce the pressure if required.

The processes according to the invention can also be carried out continuously, which is preferred for larger batches. For example, a small amount of the starting materials is initially charged in a sufficient amount of solvent for a prolonged period, the pressure is then lowered and the reaction temperature is set, and the disulfide of the formula (II) or (II') and the salt of the formula (III) are then metered in continuously or a little at a time at relatively short intervals (i.e., semicontinuously), when the resulting compound of the formula (I) or (I") begins to distill off. The disulfide and the salt can be metered in using, for example, a storage container that contains both components in mixed form. It is also possible to meter in each component on its own, from separate storage containers, and the two components can be metered in simultaneously or measured in succession at relatively short timed intervals. If appropriate, one or both components can be metered in together with the solvent used. If the operation proceeds for a relatively long period of time, it is advantageous to keep the content of the reactor substantially constant, for example, by discharging proportions of the reactor content continuously or semicontinuously, and replacing them with fresh solvent.

If required, the product of the formula (I) or (I") that is distilled off from the reaction vessel can be worked up further using customary methods. For separating off any by products that may be present and any co-distilled solvent, it is possible, for example, to re-distill fractionally. Water-soluble solvents can also be extracted using water. The alkali metal salt of an arylmercaptan formed in the bottom can be reconverted, by oxidation, into a disulfide of the formula (II) or (II'), which can then be recycled into the reaction.

The processes according to the invention have the advantages that the yields and the reaction control are noticeably improved compared to the processes of the prior art and that the process can also be employed for introducing long-chain perfluoroalkyl radicals. The process according to the invention furthermore permits continuous operation. By preparing compounds of the formula (I'), in accordance with the invention, these compounds are obtained in considerably better yields than when reacting starting materials which already contain hydroxyl, mercapto or amino substituents. These results are highly surprising.

Among the perfluoroalkyl aryl sulfides of the formula (I) that can be prepared according to the invention, 2-nitrophenyl pentafluoroethyl sulfide and 2-aminophenyl pentafluoroethyl sulfide are novel. Thus, the present invention also relates to these two compounds. With these compounds, more compounds are provided that extend the possibilities to prepare starting from perfluoroalkyl aryl sulfides—agrochemicals, pharmaceuticals, dyes, and polymers, analogously to the literature references cited at the outset.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1
2-Nitrophenyl trifluoromethyl sulfide 70 ml of dry tetramethylene sulfone were initially charged in a 250 ml three-necked flask fitted with mechanical stirrer, vacuum distillation head, and a metering funnel for solids. At 40° C. and with stirring, 7% by weight of a solid mixture (thoroughly mixed prior to filling into the metering funnel for solids) of 120 g of bis(2-nitro-phenyl) disulfide and 119 g of anhydrous potassium trifluoroacetate were then added and a vacuum was applied. At a pressure of from 200 to 230 mbar, the mixture was heated to 185 to 190° C. (bath temperature). Maintaining these conditions, the solid mixture of the reactants was metered in at a steady rate over a period of 40 min. During this time, the volatile products were collected in a receiver cooled with dry ice and having a downstream cold trap, After the reaction had ended, remaining product was distilled off by lowering the pressure to 10 mbar at 190° C. (bath temperature). The content of receiver and cold trap was poured into 250 ml of water. The organic phase was separated off to give 84 g (96% of theory) of 2-nitrophenyl trifluoromethyl sulfide (boiling point 105° C. at 12 mbar) that was pure by gas chromatography. The structure was confirmed by the $^1$H NMR, $^{19}$F NMR, and MS spectra.

Example 2
2-Aminophenyl trifluoromethyl sulfide

A solution of 25.53 g of tin(II) chloride dihydrate in 40 ml of concentrated hydrochloric acid was added dropwise to a stirred solution of 5.05 g of 2-nitrophenyl trifluoromethyl sulfide, obtained according to Example 1, in 30 ml of ethanol. After the addition had ended, the mixture was heated to 100° C. and stirred at this temperature for 1.5 hours. The mixture was cooled, ethanol was evaporated off under reduced pressure, and the residue was poured into a mixture of 150 g of ice and 150 ml of 40% strength by weight aqueous sodium hydroxide solution. The product was extracted with ether. The combined ether extracts were dried over magnesium sulfate and concentrated under reduced pressure. Vacuum distillation of the residue gave 3.31 g (75.7% of theory) of 2-aminophenyl trifluoromethyl sulfide (boiling point 102–104° C. at 50 mbar, melting point: 30–31° C.).

The structure was confined by the $^1$H NMR, $^{19}$F NMR, and MS spectra.

Particularly for larger batches or for continuous operation, the reduction can also be carried out catalytically using hydrogen.

Example 3
2Methoxyphenyl trifluoromethyl sulfide

A mixture of 6.04 g of bis(2-methoxyphenyl) disulfide, 6.60 g of anhydrous potassium trifluoroacetate, and 9 ml of dry tetramethylene sulfone was stirred in a vacuum distillation apparatus at a pressure of 65 mbar. The mixture was slowly heated in an oil bath up to a maximum of 220° C., during which time volatile products were collected in a receiver that was cooled using dry ice. Redistillation of the crude product gave 3.20 g (70% of theory) of analytically pure 2-methoxyphenyl trifluoromethyl sulfide (boiling point 80° C. at 20 mbar).

The $^{19}$F NMR data agreed with the data published in *J. Org. Chem.*, 59, 4047 (1985). The structure was additionally confirmed by the $^1$H NMR and MS spectra.

Example 4
2-Hydroxyphenyl trifluoromethyl sulfide

A mixture of 4.69 g of 2-methoxyphenyl trifluoromethyl sulfide, obtained according to Example 3, 20 ml of 48% strength by weight aqueous hydrobromic acid, and 20 ml of 96% strength by weight acetic acid was boiled under reflux for 24 hours. The completion of the reaction was then checked by gas chromatography. After cooling, the reaction mixture was poured into water. The organic phase was separated off and the aqueous phase was extracted with dichloromethane. The extract was combined with the organic phase. Drying over magnesium sulfate, concentration, and vacuum distillation gave 2.01 g (46% of theory) of 2-hydroxyphenyl trifluoromethyl sulfide (boiling point 65–66° C. at 26 mbar, melting point 35–37° C.).

The structure was confirmed by the $^1$H NMR, $^{19}$F NMR, and MS spectra.

Example 5
2-Nitrophenyl pentafluoroethyl sulfide

By the method of Example 3, a mixture of 12.24 g of bis(2-nitrophenyl) disulfide, 14.56 g of anhydrous potassium pentafluoropropionate, and 10 ml of dry tetramethylene sulfone was heated to 190° C., and the vacuum was improved during this increase in temperature from 120 mbar at 140° C. first to 50 mbar at 190° C. and then, to bring the distillation to completion, to 10 mbar at this temperature. Redistillation of the crude product gave 8.13 g (75% of theory) of the hitherto unknown 2-nitroaphnyl pentafluoroothyl sulfide (boiling point 105–107° C. at 14 mbar). Analytically pure product can be obtained by washing with water, followed by drying over magnesium sulfate maid redistillation.

$^1$H NMR (400 MHz (CDCl$_3$)): δ [ppm], J [Hz] 7.65 (td, 1H, H$^{4\ or\ 5}$, $^3J_{HH}$=7.6, $^4J_{HH}$=2.0); 7.68 (td, 1H, H$^{4\ or\ 5}$, $^3J_{HH}$=7.6, $^4J_{HH}$=2.0); 7.90 (dd, 1H, H$^6$, $^3J_{HH}$=7.6, $^4J_{HH}$=2.0); 8.00 (dd, 1H, H$^3$, $^3J_{HH}$=7.6, $^4J_{HH}$=2.0); $^{19}$F NMR (376.3 MHz (CDCl$_3$)): δ (CCl$_3$F) [ppm], J [Hz] −83.06 (t, 3F, CF$_3$, $^3J_{FF}$=3.5); −91.12 (q, 2F, CF$_2$, $^3J_{FF}$=3.5); MS: [m/z] 273 M$^+$; 154 (M-CF$_2$CF$_3$)$^+$; 108 C$_6$H$_4$S$^+$; 96 C$_5$H$_4$S$^+$; 69 CF$_3^+$;

| C/H/N analysis [%]: | C | H | N |
| --- | --- | --- | --- |
| calc. for C$_8$H$_4$O$_2$NF$_5$S: | 35.17 | 1.48 | 5.13 |
| found: | 35.4 | 1.5 | 5.3 |

Examnple 6
2-Aminophenyl pentafluoromethyl sulfide

By the method of Example 2, 6.26 g of 2-nitrophenyl pentafluoroethyl sulfide (obtained according to Example 5 and initially charged in 30 ml of ethanol) and 25.85 g of tin(II) chloride dihydrate in 40 ml of concentrated hydrochloric acid gave, after distillation, 4.5 g (81% of theory) of the hitherto unknown 2-aminophenyl pentafluoroethyl sulfide (boiling point 77° C. at 12 mbar).

$^1$H NMR (400 MHz (CDCl$_3$)): δ [ppm], J [Hz] 4.38 (ws, 2H, NH$_2$), 6.70 (m, 2H, H$^3$, H$^{4\ or\ 5}$); 7.24 (td, 1H, H$^{4\ or\ 5}$, $^3J_{HH}$=7.6, $^4J_{HH}$=1.5); 7.43 (dd, 1H, H$^6$, $^3J_{HH}$=7.6, $^4J_{HH}$=1.5); $^{19}$F NMR (376.3 MHz (CDCl$_3$)): δ(CCl$_3$F) [ppm], J [Hz]-83.24 (t, 3F, CF$_3$, $^3J_{FF}$=3.5); −92.18 (q, 2F, CF$_2$, $^3J_{FF}$=3.5); MS: [m/z] 243 M$^+$; 124 (M-CF$_2$CF$_3$)$^+$; 80 C$_5$H$_6$N$^+$;

| C/H/N analysis [%]: | C | H | N |
|---|---|---|---|
| calc. for C$_8$H$_6$NF$_5$S: | 39.51 | 2.49 | 5.76 |
| found: | 39.70 | 2.60 | 5.90 |

Example 7
4-Trifluoromethylphenyl trifluoromethyl sulfide

By the method of Example 3, a mixture of 12.10 g of bis(4-trifluorophenyl)disulfide, 10.39 g of anhydrous potassium trifluoroacetate, and 10 ml of dry tetramethylene sulfone was heated to 195° C., and the vacuum was simultaneously improved from 120 mbar to 50 mbar. This gave 12.61 g of crude distillate which were subsequently poured into water. The organic phase was separated off, dried over magnesium sulfate, and redistilled, giving 5.24 g (63% of theory) of 4-trifluoromethylphenyl trifluoromethyl sulfide of boiling point 99–100° C. at 195 mbar and melting point 30–31° C. The structure was confirmed by the $^1$H NMR, $^{19}$F NMR, and MS spectra.

Example 8
2-Chloro-5-nitrophenyl trifluoromethyl sulfide

By the method of Example 1, 45.43 g of bi-(2-chloro-5-nitrophenyl) disulfide were reacted with 36.64 g of anhydrous potassium trifluoroacetate and 25 ml of dry tetramethylene sulfone, and the product was worked up to give 17.23 g of a mixture of 7% of 2-fluoro-5-nitrophenyl trifluoromethyl disulfide and 93% of 2chloro-5-nitro-phenyl trifluoromethyl sulfide (GC analysis). Distillation of the crude product gave pure 2-chloro5-nitrophenyl trifluoromethyl sulfide (boiling point 126–129° C. at 16 mbar). The structure was confirmed by the $^1$H NMR, $^{19}$F NMR, and MS spectra.

Example 9
5-Amino-2-chlorophenyl trifluoromethyl sulfide

By the method of Example 2, 7.76 g of 2-chloro-5-nitrophenyl trifluoromethyl sulfide (obtained according to Example 8) in 40 ml of ethanol and 33.98 g of tin(II) chloride dihydrate in 50 ml of concentrated hydrochloric acid gave, after evaporation of the diethyl ether, 5.75 g (84% of theory) of 5-amnino-2chlorophenyl trifluoromethyl sulfide (boiling point 131–133° C. at 16 mbar) that was pure by gas chromatography. The structure was confirmed by the $^1$H NMR, $^{19}$F NMR, and MS spectra.

Example 10
(comparison)

By the method of *Tetrahedron Lett.*, 37, 9057 (1996), a mixture of 9.15 g of bis(2-nitrophenyl) disulfide, 9.15 g of anhydrous potassium trifluoroacetate, and 15 ml of dry tetramethylene sulfone was heated to 230° C. with stirring in a distillation apparatus at atmospheric pressure, and volatile products were collected in a receiver which was cooled with dry ice (−78° C.). The crude product was poured into water. Phase separation gave 1.63 g (24.6% of theory) of crude 2-nitrophenyl trifluoromethyl sulfide.

What is claimed is:
1. 2-Nitrophenyl pentafluoroethyl sulfide.
2. 2-Aminophenyl pentafluoroethyl sulfide.

* * * * *